United States Patent
Goodwin

(10) Patent No.: US 9,651,493 B2
(45) Date of Patent: May 16, 2017

(54) SYSTEMS AND METHODS FOR CAMERA-BASED IMAGE PROCESSING IN MICROSCOPY INSTRUMENTS

(75) Inventor: Paul C. Goodwin, Issaquah, WA (US)

(73) Assignee: GE HEALTHCARE BIO-SCIENCES CORP., Marlborough, MA (US)

(*) Notice: Subject to any disclaimer, the term of this patent is extended or adjusted under 35 U.S.C. 154(b) by 504 days.

(21) Appl. No.: 13/978,800

(22) PCT Filed: Jan. 11, 2012

(86) PCT No.: PCT/SE2012/050011
§ 371 (c)(1),
(2), (4) Date: Jul. 9, 2013

(87) PCT Pub. No.: WO2012/096619
PCT Pub. Date: Jul. 19, 2012

(65) Prior Publication Data
US 2013/0300853 A1    Nov. 14, 2013

Related U.S. Application Data

(60) Provisional application No. 61/432,015, filed on Jan. 12, 2011.

(51) Int. Cl.
*G01N 21/64* (2006.01)

(52) U.S. Cl.
CPC ..... *G01N 21/6458* (2013.01); *G01N 21/6408* (2013.01); *G01N 21/6428* (2013.01)

(58) Field of Classification Search
CPC ............ G01N 21/64; G01N 21/6408; G01N 21/6428; G01B 21/06; G03B 17/48
See application file for complete search history.

(56) References Cited

U.S. PATENT DOCUMENTS 6,166,385 A * 12/2000 Webb ................ G02B 21/0084
                                                        250/458.1
2004/0081621 A1* 4/2004 Arndt .................. A61B 5/0059
                                                        424/9.6
(Continued)

FOREIGN PATENT DOCUMENTS

JP         2002508076 A     3/2002
JP         2011-519038 A    6/2011
(Continued)

OTHER PUBLICATIONS

Bates, M., et al., American Association for the Advancement of Science, vol. 317, No. 5845, 2007, 1749-1753.
(Continued)

*Primary Examiner* — Jay Patel
*Assistant Examiner* — Marnie Matt

(57) ABSTRACT

Systems and methods for executing super-resolution microscopy of a specimen with most of the image processing performed in a camera of a fluorescence microscopy instrument are described. In one aspect, the camera includes one or more processors to execute machine-readable instructions that control excitation light output from a multi-channel light source, control capture of intermediate images of the specimen, and perform image processing of the intermediate images to produce a final super-resolution image of the specimen.

29 Claims, 12 Drawing Sheets

(56) References Cited

U.S. PATENT DOCUMENTS

| | | | |
|---|---|---|---|
| 2005/0146784 A1* | 7/2005 | Vogt | G02B 21/0076 359/368 |
| 2008/0068588 A1* | 3/2008 | Hess | G01N 21/6458 356/36 |
| 2008/0315119 A1* | 12/2008 | Blackmore | G01N 21/6428 250/459.1 |
| 2009/0237501 A1* | 9/2009 | Lemmer | G01N 21/6428 348/79 |
| 2009/0310213 A1 | 12/2009 | Hing et al. | |
| 2011/0117025 A1* | 5/2011 | Dacosta | A61B 5/0059 424/9.6 |
| 2011/0149097 A1* | 6/2011 | Danuser | G01N 21/636 348/222.1 |
| 2011/0233382 A1* | 9/2011 | Solin | H01L 27/14665 250/208.1 |
| 2011/0297847 A1* | 12/2011 | Courtney | G01N 21/6428 250/459.1 |
| 2014/0312247 A1* | 10/2014 | McKee | G01N 21/6456 250/459.1 |

FOREIGN PATENT DOCUMENTS

| | | | |
|---|---|---|---|
| WO | 9901745 A1 | 1/1999 | |
| WO | WO 9901745 A1 * | 1/1999 | A61B 5/0088 |
| WO | WO 2009/132811 | 11/2009 | |
| WO | WO 2010/037486 | 4/2010 | |
| WO | WO 2010/060545 | 6/2010 | |
| WO | WO 2010/082048 | 7/2010 | |

OTHER PUBLICATIONS

English language translation of Japanese Office Action regarding Japanese Application No. 2013-549387 dated Oct. 28, 2015, 3 pages.

* cited by examiner

SYSTEMS AND METHODS FOR CAMERA-BASED IMAGE PROCESSING IN MICROSCOPY INSTRUMENTS

CROSS-REFERENCE TO A RELATED APPLICATION

This application is a filing under 35 U.S.C. 371 of international application number PCT/SE2012/050011, filed Jan. 11, 2012, published on Jul. 19, 2012 as WO 2012/096619, which claims the benefit of Provisional Application No. 61/432,015; filed Jan. 12, 2011.

TECHNICAL FIELD

This disclosure relates to fluorescence microscopy, and in particular, to systems and methods used to perform fluorescence microscopy.

BACKGROUND

In recent years, a number of techniques have been developed to increase the resolution of light microscopy beyond the diffraction limit Some of these techniques involve stochastically activating the fluorescence of a subset of molecules that are present in a field-of-view, capturing an image of those molecules that are activated with a digital camera, transferring the image to a computer, and then reversibly or irreversibly deactivating the fluorescence of the molecules. This process is repeated for a large number of cycles until the pool of nearly all of the molecules present have been adequately sampled, which may take 40,000 cycles or more. Each image of this large number of images is then analyzed by fitting either single Gaussian distributions or overlapping Gaussians to fluorophore-image centroids or spots. The locations and probabilities of fit for each molecule are then determined by successively storing each image in the computer's memory, performing a cross-correlation of the fits of the Gaussians, and then storing the location and confidence of fit for each molecule. While acquisition of the images can be accomplished relative quickly, handling and processing such a large number of images is relatively slow because these techniques necessitate acquiring and processing a large amount of image data in order to obtain a relatively small number of pixel locations. For example, 40,000 cycles are used to capture 40,000 separate images which results in processing 20 gigabytes of data in order to generate a single 256 kilobyte final image. For these reasons, engineers, scientists, and microscope manufacturers continue to seek less computationally demanding systems and methods for handling and processing the images.

SUMMARY

Various systems and methods for executing super-resolution microscopy of a specimen with most of the image processing performed in a camera of a fluorescence microscopy instrument are described. In one aspect, the camera includes one or more processors to execute machine-readable instructions that control excitation light output from a multi-channel light source, control capture of intermediate images of the specimen, and perform image processing of the intermediate images to produce a final super-resolution image of the specimen.

DETAILED DESCRIPTION

Systems and methods for executing super-resolution microscopy of specimen within the camera of a fluorescence microscopy instrument greatly reduces the amount of data that is typically transferred to the instrument computer, which reduces the amount of data storage used by the computer and eliminates the need for a high-speed interface between the camera and the computer. In addition, by performing most of the image processing within the camera and avoiding a large number of data transfers from the camera to the computer, the overall performance of the fluorescence microscope instrument is improved.

Figure 1:
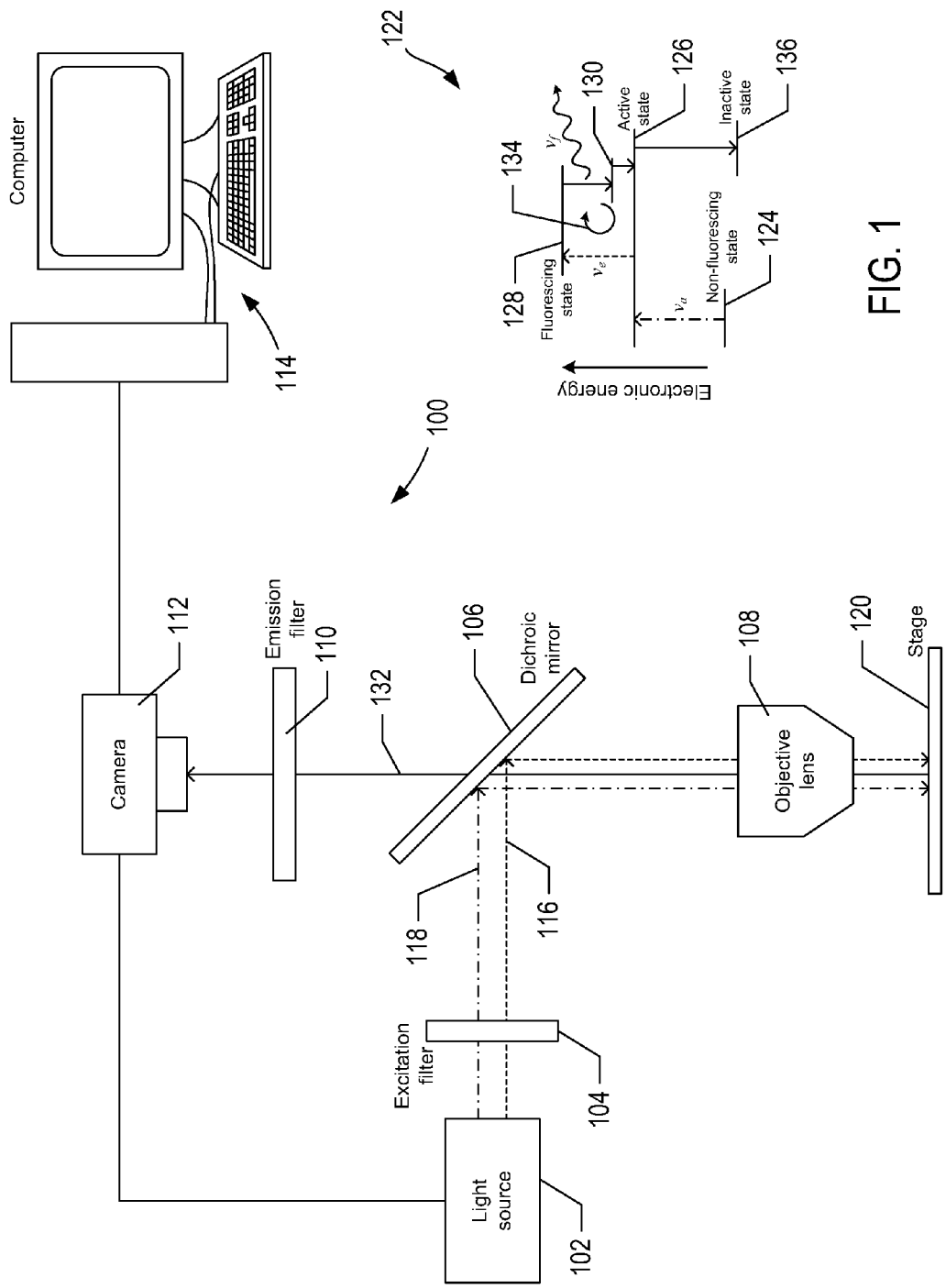
FIG. 1 shows a schematic representation of an example fluorescence microscopy instrument to perform super-resolution microscopy.

FIG. 1 shows a schematic representation of an example fluorescence microscopy instrument 100 used to perform super-resolution microscopy. The instrument 100 includes a light source 102, an excitation filter 104, a dichroic mirror 106, an objective lens 108, an emission filter 110, a camera 112, and a computer 114. The light source 102 can be configured with a number of separate lasers, each laser to emit a substantially monochromatic beam of light of a single wavelength or light within a narrow band of wavelengths of the electromagnetic spectrum. The light emitted by each laser is commonly referred to as a "channel." For example, as shown in FIG. 1, the source 102 emits two different beams of excitation light represented by differently patterned lines 116 and 118. The beams 116 and 118 pass through the excitation filter 104, which narrows the wavelength range of each beam. The dichroic mirror 106 reflects the beams 116 and 118 into the objective lens 108 which directs the beams into a specimen (not shown) disposed on a stage 120. The specimen may be composed of a number of different components, many of which are labeled with fluorescent probes. The beam 116 can be an activation beam with a frequency that converts the fluorophores into an activate state, and the beam 118 can be an excitation beam with a different frequency that causes the fluorophores in the active state to fluoresce. A portion of the fluorescent light emitted from the fluorophores is collected and collimated by the objective lens 108 into a beam 132. The dichroic mirror 106 allows transmission of the beam 132, and the emission filter 110 removes stray excitation light from the beam 132. The fluorescent light is captured by the camera 112 to create a single image of the specimen. As shown in FIG. 1, the camera 112 is electronically connected to the light source 102 and the computer 114. The camera 112 is configured to control operation of the light source 102 and to process captured images of the specimen as described below. In particular, the camera 112 controls operation of the light source 102 in order to execute super-resolution fluorescence microscopy described below. FIG. 1 also shows the camera 112 electronically connected to the computer 114. In certain embodiments, the camera 112 executes super-resolution fluorescence microscopy by directing the capture and processing of all the images of the specimen into a final super-resolution image that is sent to the computer 114 for storage and/or display as described in greater detail below. Alternatively, the camera 112 and the computer 114 can split processing of the images as also described in greater detail below.

The fluorophores used to label components of the specimen typically have a number of different electronic states, an example of which is represented in FIG. 1 by an electronic band diagram 122. When the fluorophores are introduced to the specimen, the fluorophores are attached to probes that bind to components of the specimen. The fluorophores are initially in a non-fluorescing, dark state which can be a ground state with electronic energy 124. In super-resolution microscopy, intermediate images of the specimen are captured by the camera 112. The camera 112 directs the light source 102 to emit the activation beam 116 with a frequency, $v_a$, for a brief period of time and with a very low intensity in order to stochastically convert a relatively small number of fluorophores into the active state with electronic energy 126. The camera 112 then directs the light source 102 to turn "off" the beam 116 and emit the beam 118 with a frequency, $v_e$, that converts only the subset of fluorophores already in the active state into a fluorescing state with electronic energy 128. In the example of FIG. 1, the fluorophores in the fluorescing state emit fluorescent excitation light with a frequency, $v_f$, when transitioning to a lower energy 130 intermediate state followed by thermal relaxation back to the active state. In certain embodiments, when the camera 112 has finished capturing an image of the fluorescing fluorophores, the camera 112 directs the light source 102 to continue emitting the beam 118 for a period of time sufficient to cause the activated fluorophores to undergo hundred, thousands or more excitation/emission cycles represented by directional arrow 134. The fluorophores under continued illumination by the excitation beam 118 ultimately transition to a bleached or an inactive state represented by energy level 136. Alternatively, the light source 102 can emit a third beam of light (not shown) the converts the fluorophores from the active state into the inactive state. Converting fluorophores from the active state into the inactive state can be a complete or partial reconfiguring of the fluorophore into a molecule that is not able to transition to the active state or the fluorescing state when illuminated by either of the beams 116 and 118.

Figure 2A:
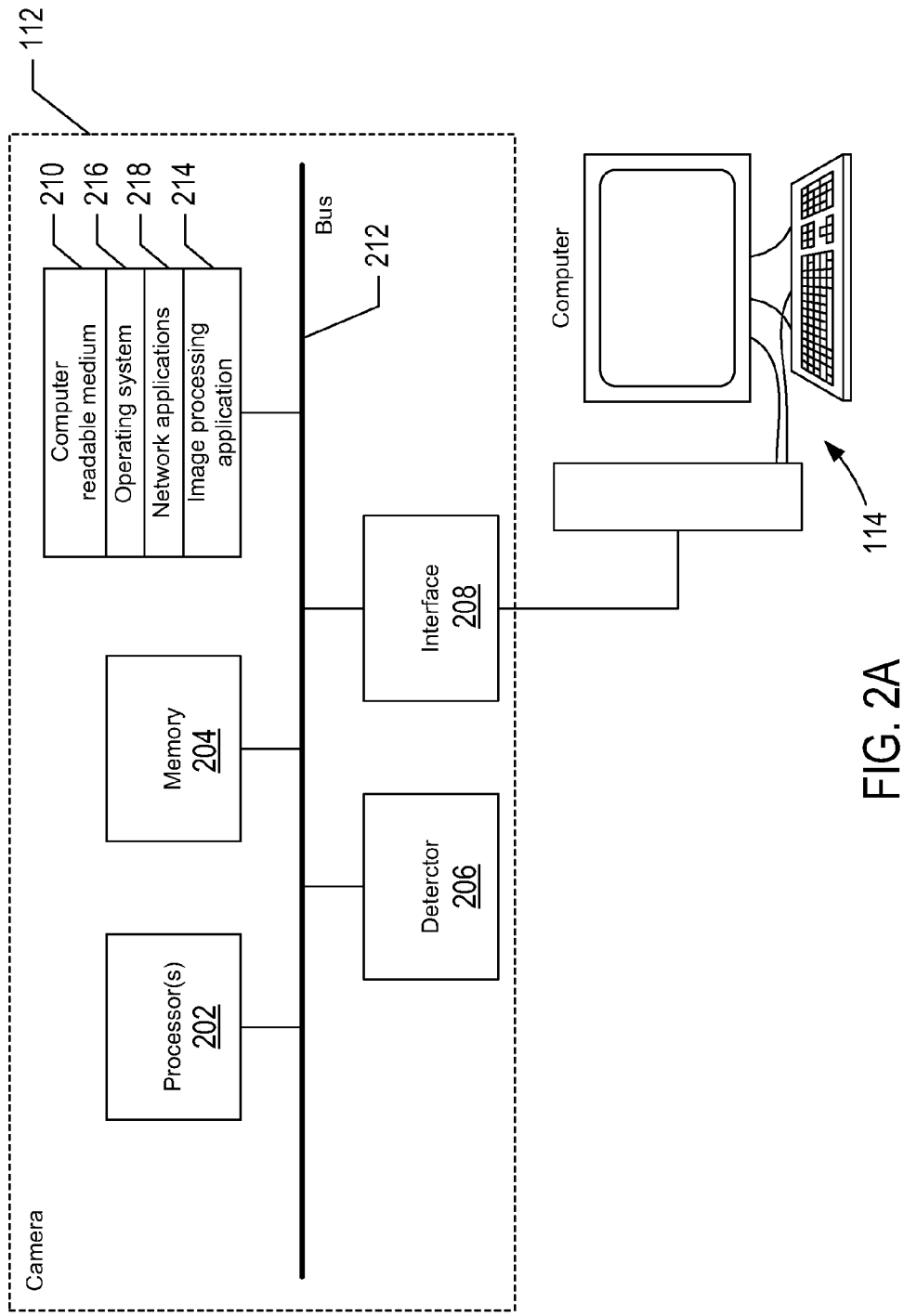
FIGS. 2A-2C show schematic representations of three different example implementations of a camera.
Figure 2B:
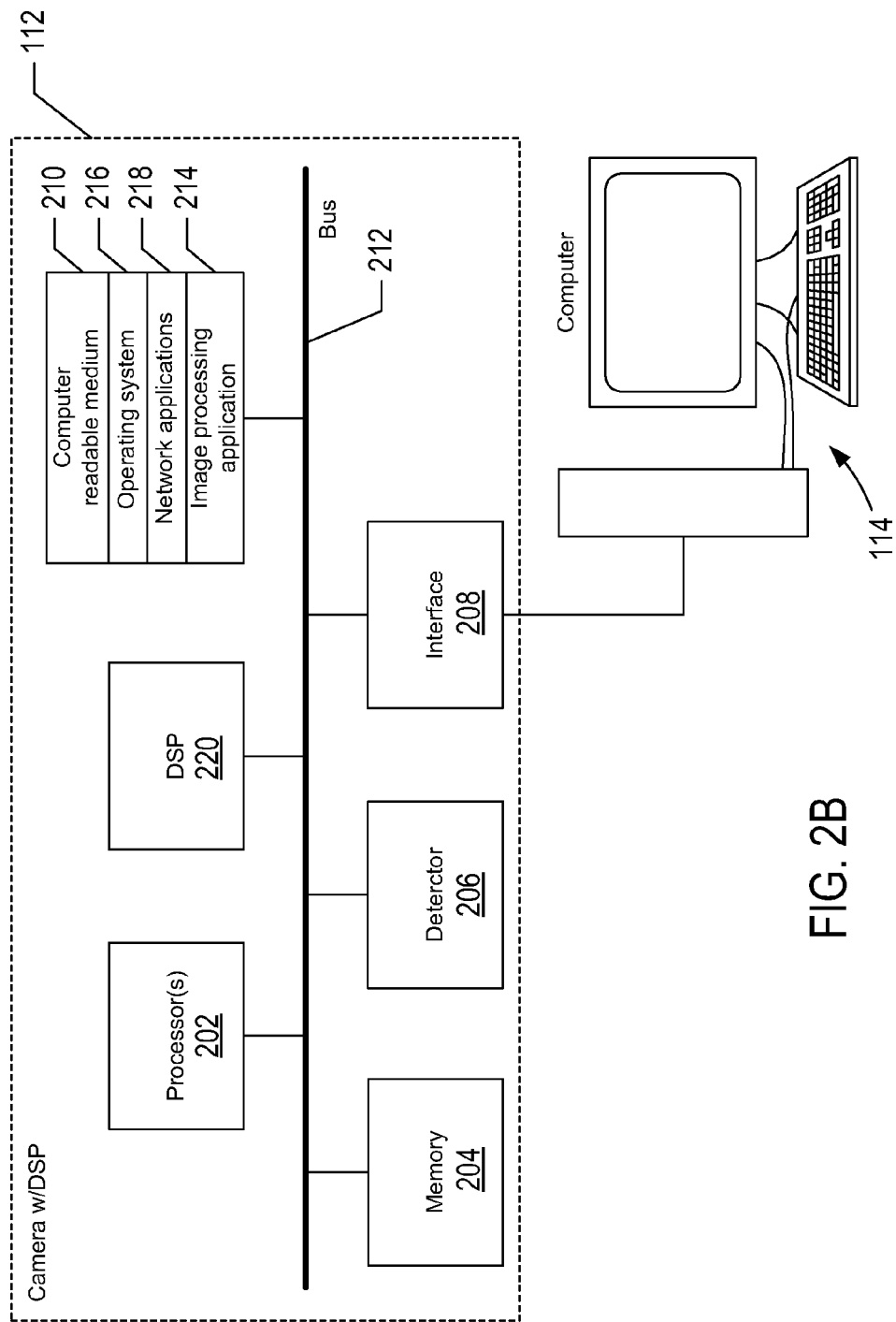
Figure 2C:
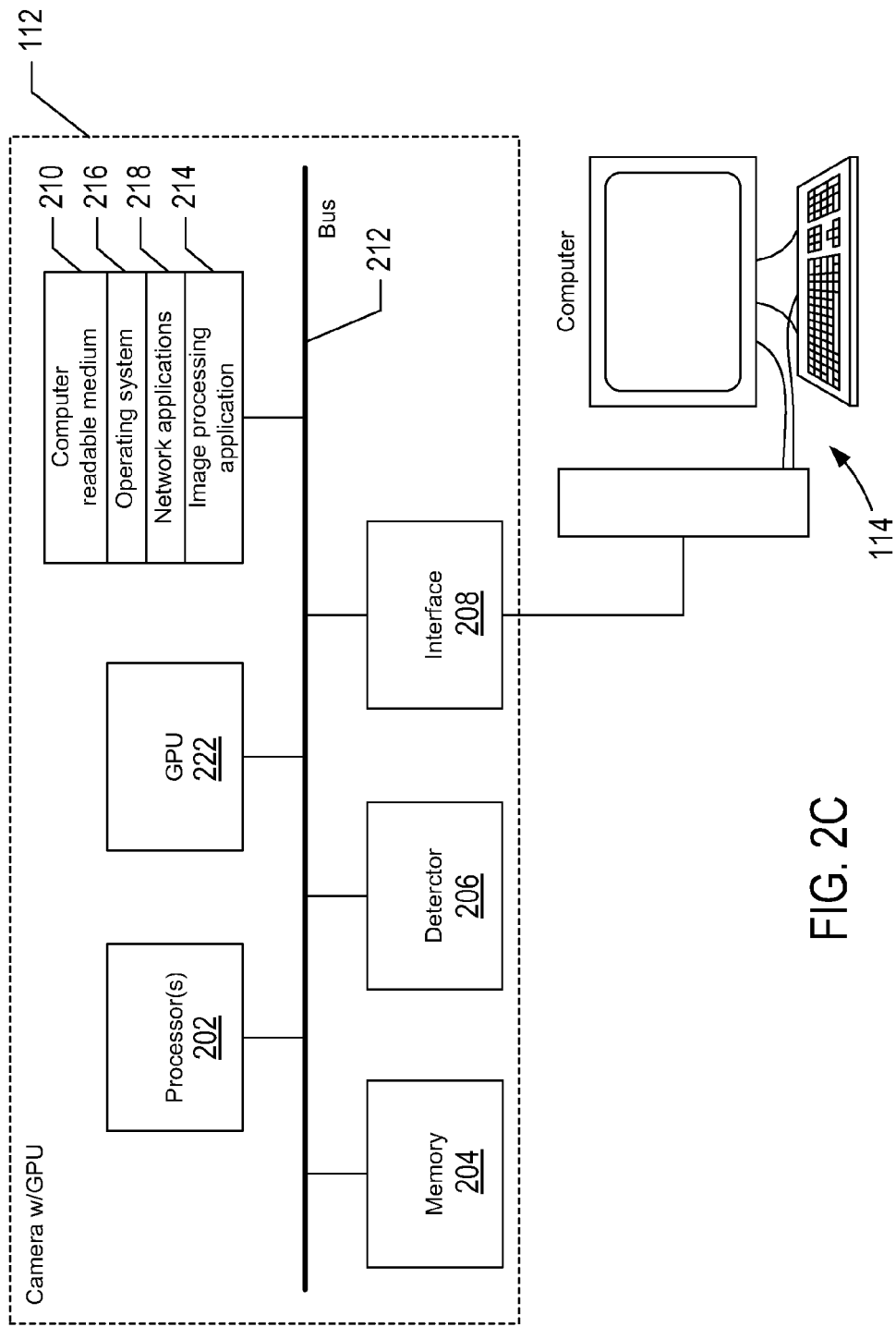

The camera 112 can be a computing device that operates the lights captures, stores intermediate images, and processes the intermediate images to produce a final super-resolution image. FIGS. 2A-2C show schematic representations of example implementations of the camera 112. In the example of FIG. 2A, the camera 112 includes one or more processors 202, memory 204, a detector 206, a video or camera interface 208, and one or more computer-readable mediums 210. Each of these components is operatively coupled to one or more buses 212. The processor 202 can be a single of multi-core processor with internal memory. The memory 204 can be main memory such as DRAM or SRAM or any other suitable memory. The detector 206 can be an array or photodetectors including an array of CMOS detectors or an array of CCD detectors. The interface 208 can be a Local Area Network ("LAN"), a wireless LAN, a 4G mobile wide area network ("WAN") or a WiMax WAN. The computer-readable medium 210 can be any suitable non-transitory medium that participates in storing and providing machine-readable instructions to the processor 202 for execution. For example, the computer-readable medium 210 can be a magnetic disk, flash memory, an optical disk, or a magnetic disk drive. The computer-readable medium 210 can also store machine-readable instructions 214 directed to super-resolution fluorescent microscopy image processing described below. The computer-readable medium 210 may also store an operating system 216 and network machine-readable instructions 218. The operating system 216 can be multi-user, multiprocessing, multitasking, multithreading, and real-time and can perform tasks such as recognizing input from input devices, recognizing input from a keyboard, a keypad, or a mouse; sending output to the computer 114; keeping track of files and directories on the medium 210; controlling peripheral devices such as disk drives, monitors and printers; and managing traffic on the one or more buses 212. The network applications 218 includes various components for establishing and maintaining network connections, such as machine-readable instructions for implementing communication protocols including TCP/IP, HTTP, Ethernet, USB, and FireWire. Alternatively, FIG. 2B shows an example of the camera 112 that includes a digital signal processor ("DSP") 220 coupled to the bus 212 to process the intermediate images to produce a final super-resolution image as described below. The DSP 220 may have multiple processors, multi-ported local memory and input/output control. The DSP 220 is able to transfer data to and from the memory 204 and the I/O controller while simultaneously processing data from local memory. In order to map machine-readable instructions into the DSP 220 architecture, blocks of data in memory 204 are broken into smaller subsets for processing in the DSP 220 processors. Alternatively, FIG. 2C shows an example of the camera 112 that includes a graphics processing unit ("GPU") 222 coupled to the bus 212 to process the intermediate images to produce a final super-resolution image as described below. The GPU 222 is a specialized computing device designed to rapidly manipulate and alter memory to accelerate the processing of images. Alternatively, the camera 112 can include application-specific integrated circuit ("ASIC") coupled to the bus 212 that is customized to process the intermediate images to produce a final super-resolution image as described below.

Figure 3:
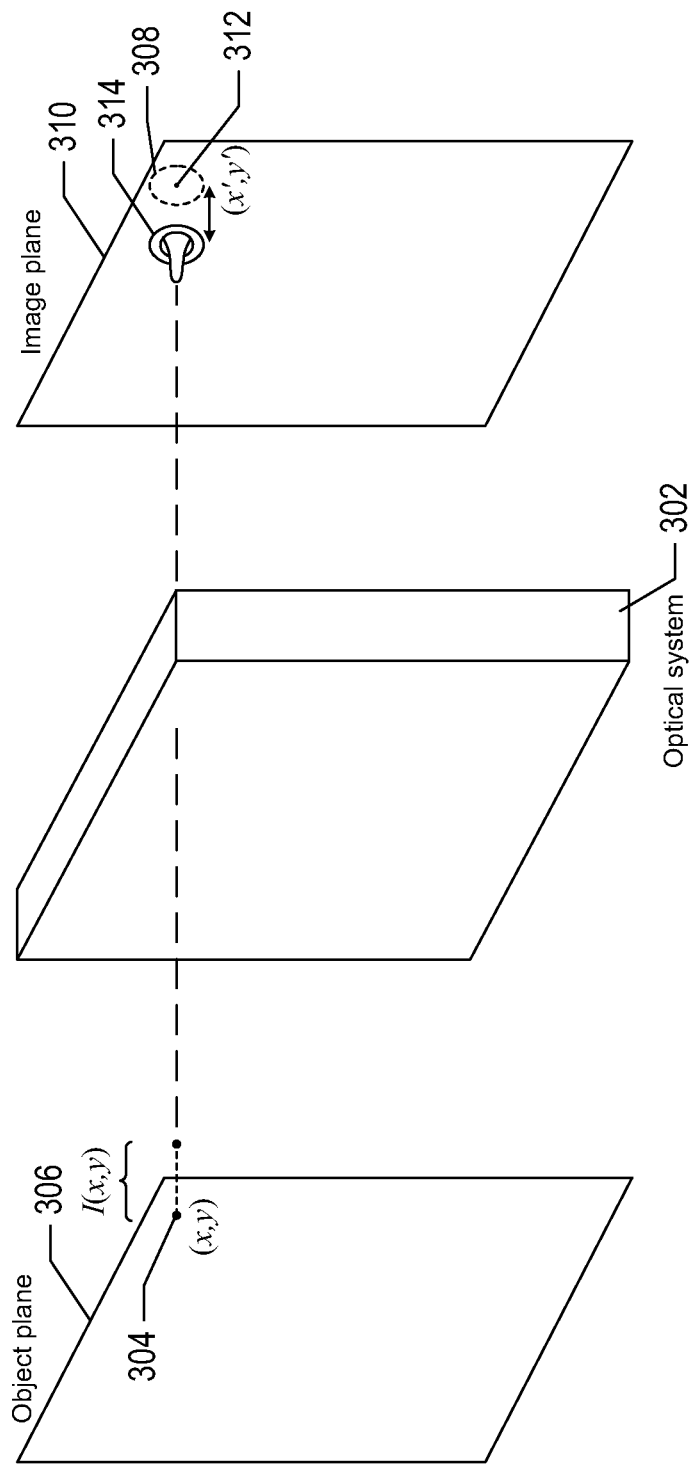
FIG. 3 shows an optical system that receives light output from a point source in an object plane and spreads out to produce a spot in a corresponding image plane.

The camera 112 alone or the camera 112 in combination with the computer 114 can execute any of various super-resolution fluorescent microscopy techniques that have been developed to allow imaging of fluorophore-labeled specimens at resolutions significantly below diffraction-limited resolution. These techniques are typically based on collecting a series of intermediate images of fluorescent light emitted from different subsets of fluorophore-labeled components of a specimen over time, provided the emitting fluorophores are separated from one another by distances greater than approximately 200 nm. In other words, provided the positions of the emitting fluorophores in the specimen can be resolvable by traditional optical microscopy, the positions of the fluorophores in a specimen can be determined, in certain cases, to a resolution of below 10 nm. However, because the fluorescent-emission signal can be interpreted only when the emitting fluorophores are sparsely arranged within the sample, a large number of intermediate images are produced from different subsets of sparse, stochastically distributed, activated fluorophores in order to construct a final super-resolution image of a fluorophore-labeled specimen. Each intermediate image captured by the camera 112 is a diffraction-limited image of a subset of sparsely arranged fluorophores. The light passing through the optical system of the camera 112 and the microscope causes the light to deviate from straight-line propagation and spread out somewhat in the image plane of the camera 112, which is located at the detector 206. The optical system can be the camera lens and other optical components of the microscope that direct and focus light from an object plane of the specimen onto the image plane of the camera 112. When an optical system with a circular aperture receives plane waves output from a point source in the object plane, such as a fluorescent light emitting fluorophore, rather than there being a corresponding bright narrowly defined image point in the image plane, the light actually spreads out into a circular spot called an Airy disk composed of alternating light and dark rings. FIG. 3 show a representation of an example optical system 302 of a microscope that receives light output from a point source (x, y) 304 in an object plane 306 of a specimen. For example, the point source 304 can be a fluorescing fluorophore. The optical system 302 spreads the light out to produce a spot 308 in a corresponding image plane 310 of the camera. The light output from the point source 304 has an intensity I(x, y) that is transformed by the optical system 302 into the spot 308 centered about a point (x', y') 312 with a corresponding intensity distribution represented by a symmetrical Airy disk 314 over the spot 308.

Figure 4:
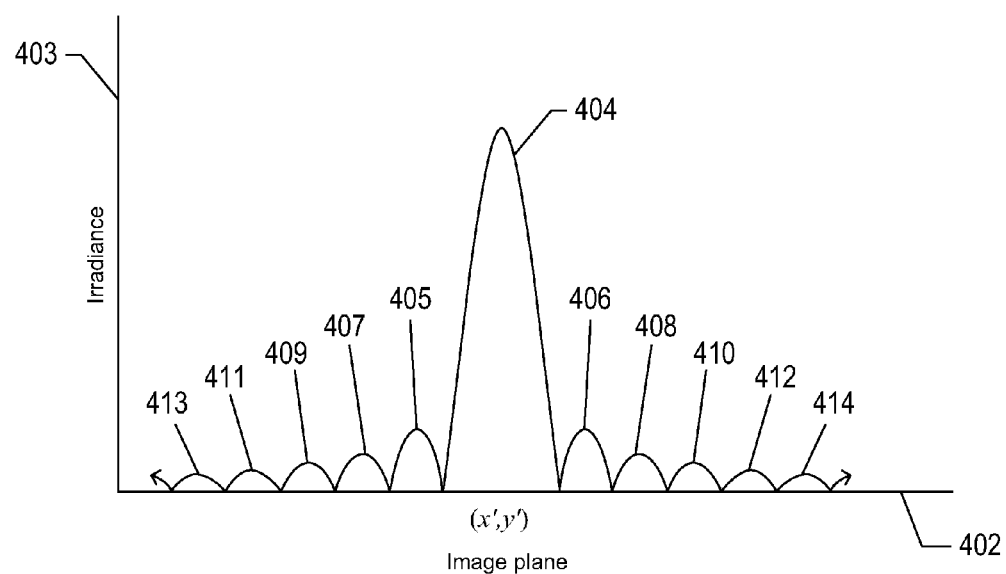
FIG. 4 shows an example representation of an Airy disk in one dimension of an image plane.

FIG. 4 shows an example representation of an Airy disk in one dimension within an image plane. Horizontal axis 402 is a line in the image plane passing through a point (x', y') in the image plane, such as the point 312 shown in FIG. 3, and vertical axis 403 represents intensity. The Airy disk has a tall, relatively narrow central peak 404 with secondary peaks of decreasing height 405-414 extending outward away from the central peak. The height of the curve corresponds to intensity. Any point on the surface of the Airy disk corresponds to the intensity observed at a corresponding position on the image plane. In other words, an image produced by an optical system of a point source in the object plane appears as a central bright disk, corresponding to the central peak 404 of the Airy disk, with concentric rings of light of increasing radius corresponding to the rings or ridges surrounding the central peak.

Figure 5:
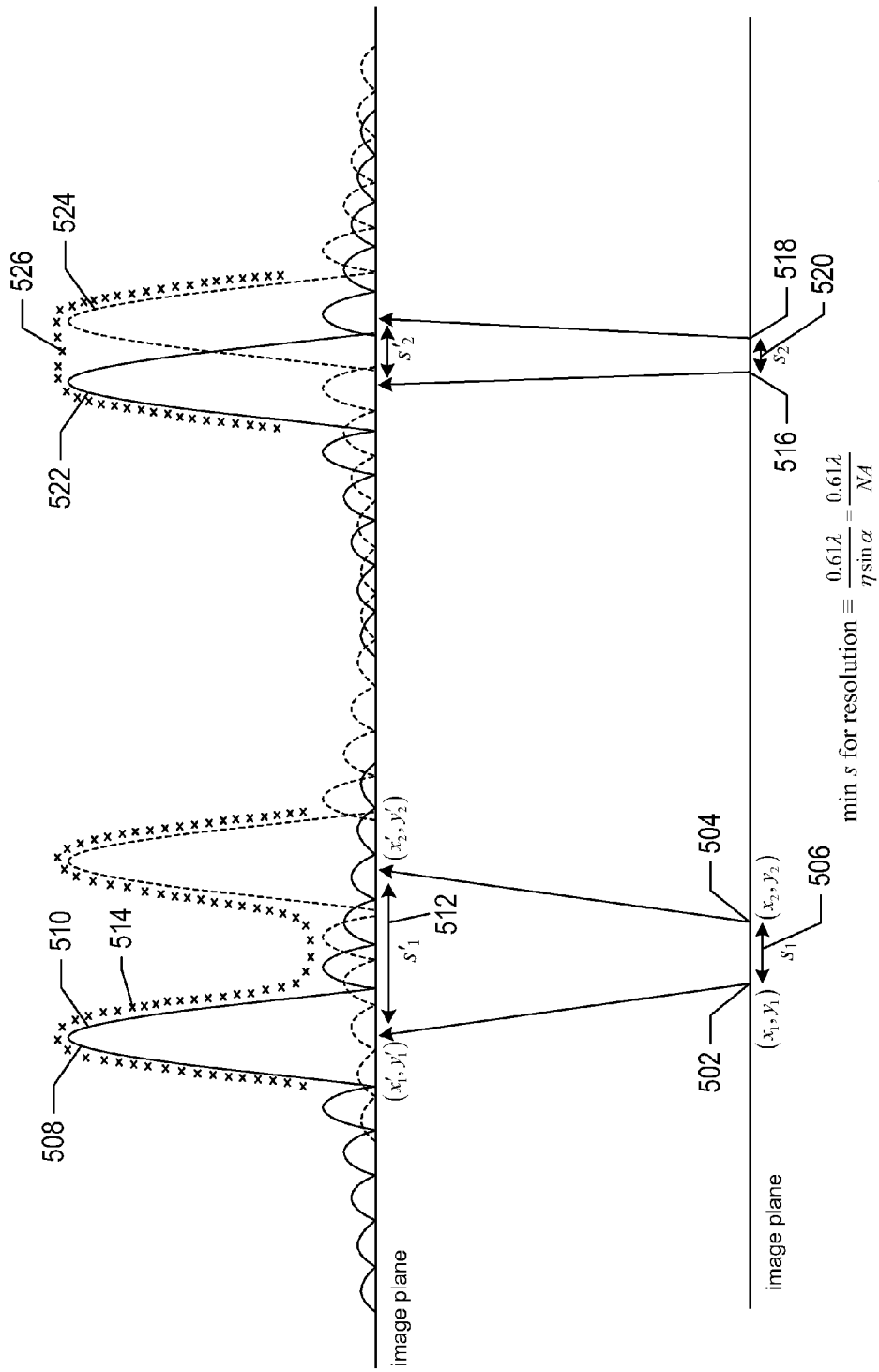
FIG. 5 shows a diffraction limit associated with an optical system.

The radius of the Airy disk determines the overlapping of neighboring Airy disks and therefore the diffraction limit of the image. FIG. 5 shows the diffraction limit associated with an optical system. Consider two points $(x_1, y_1)$ 502 and $(x_2, y_2)$ 504 in an object plane separated by a distance $s_1$ 506. The images of these two points output from an optical system appear as two Airy disks 508 and 510 centered at image points $(x'_1, y'_1)$ and $(x'_2, y'_2)$. The spreading of light from point sources 502 and 504 into spots with intensity distributions represented by the disks 508 and 510 in the image plane is a diffraction-related phenomenon. When $s_1$ is sufficiently large that the corresponding distance $s'_1$ 512 between the centers of the disk 508 and 510 in the image plane separates the Airy disk so that the sum of the two Airy disks, represented in FIG. 5 by curve 514, remains clearly bimodal, the images of the points 502 and 504 in the image plane can be distinguished from one another. However, when two points 516 and 518 in the object plane are separated by a sufficiently small distance $s_2$ 520 that the corresponding images 522 and 524 of the two points in the image plane overlap, with the sum of the two Airy disks, represented by curve 526, merging into a single peak, the two points 516 and 518 cannot be distinguished from one another in the image plane. The minimum spacing, or maximum resolution, for traditional optical microscopy is generally regarded as:

$$\frac{0.61\lambda}{\eta \sin\theta} = \frac{0.61\lambda}{NA}$$

where $\theta$ is the half-angle of the maximum cone of light that can enter or exit the optical system;
$\lambda$ is the wavelength of light;
$\eta$ is the index of refraction of the medium in which the optical system is operating; and
NA is the numerical aperture of the microscope objective.
The minimum spacing, or maximum resolution, in the input image corresponds to spacing between Airy disk at which the first left-hand zero point of the right-hand disk coincides with the first right-hand zero point of the left-hand disk. The minimum separation, or maximum resolution, of any two adjacent fluorescing fluorophores that can be imaged corresponds to about 200 nm for optical microscopy systems. The minimum spacing, or maximum resolution, is referred to as "the diffraction limit," since the Airy disk images of point sources in the image plane arise as a result of diffraction.

In order to ensure that the density of fluorophores simultaneously activated at any point in time is such that any pair of activated fluorophore is separated by at least 200 nm, the camera 112 operates the light source 102 to emit the activation beam 116 with a very low intensity so that very few photons with energy $\hbar v_a$ reach the object plane. The few photons that do reach the object plane only excite a subset of the fluorophores and the fluorophores that are excited are stochastically distributed over the object plane so that the likelihood of any two photons activating two fluorophores separated by less than 200 nm is very low. As a result, the image captured by the camera 112 is composed of a sparse distribution of ideally non-overlapping Airy disks.

Figure 6:
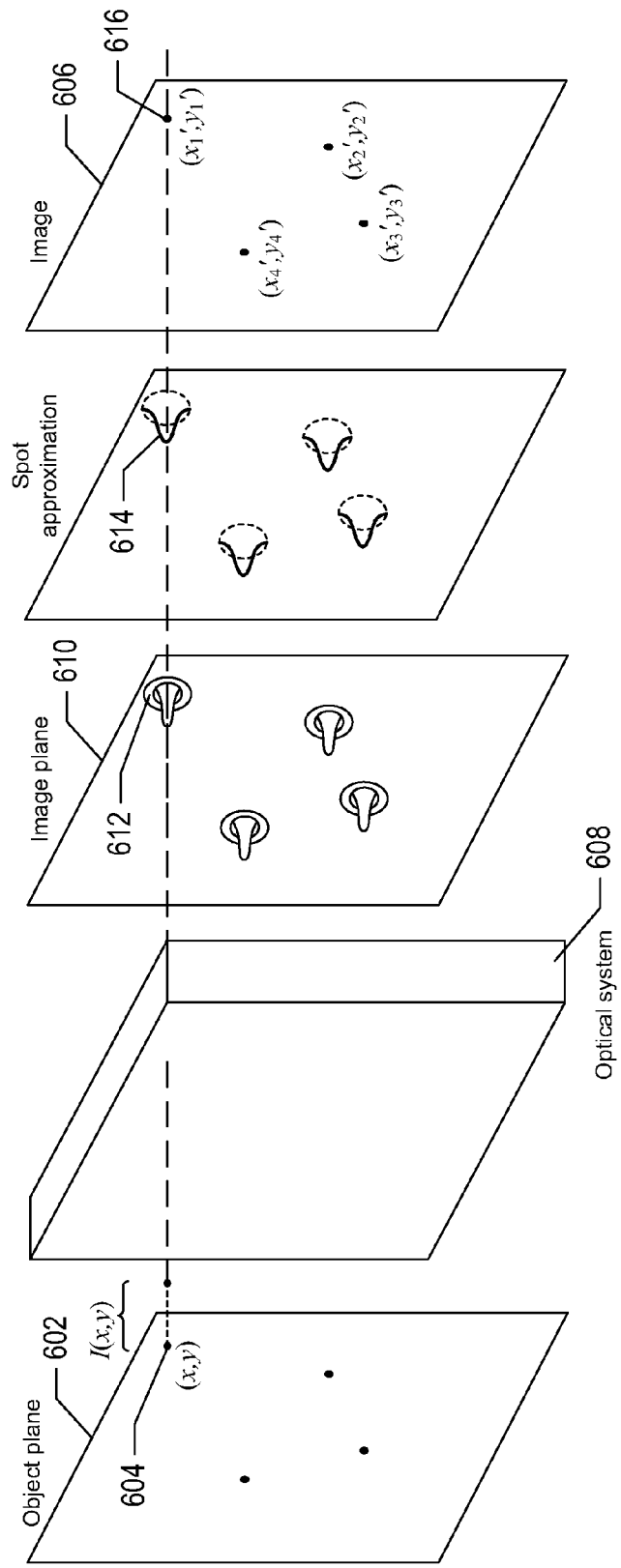
FIG. 6 shows processing of a sparse, stochastic distribution of point sources in an object to produce an image in an image plane.

FIG. 6 shows an example object plane 602 of a sparse stochastic distribution of four fluorescing fluorophores 604 and a representation of a process used to produce a resulting super-resolution image 606 of the four fluorescing fluorophores. The sparse stochastic distribution of fluorescing fluorophores in the object plane 602 is produced by exciting the specimen with a very low intensity beam 116 as described above. The optical system 608 of the camera 112 receives light output from each fluorescent point source in the object plane 602, such as fluorescent point source (x, y) 404, and spreads the light out to produce four corresponding spots in a corresponding image plane 610, such as spot 612. The intensity distribution of each spot in the image plane 610 is characterized by an Airy disk that corresponds to the fluorescing point source 604, such as an Airy disk at the spot 612. The camera 112 processes the image by curve fitting a two-dimensional Gaussian distribution to each spot. For example, curve 614 represents a Gaussian distribution curve fit to the spot 612. The (x', y') coordinates associated with the maximum of each Gaussian distribution are taken as the centroid coordinates of each spot. The resulting super-resolution image 606 is produced by assigning an intensity value to each centroid obtained in the spot approximation. For example, centroid coordinates $(x'_1, y'_1)$ correspond to the maximum of the Gaussian distribution 614, and the intensity value associate with the centroid coordinates ($x'_1$, $y'_1$) 616 forms a pixel in the image 606 that corresponds to the fluorescing fluorophore located at the point 604 in the object plane 602. The resulting image 606 is a super-resolution, intermediate image of sparse, stochastically distributed pixels that correspond to the point sources in the object plane 602. The camera can store the image data.

Figure 7:
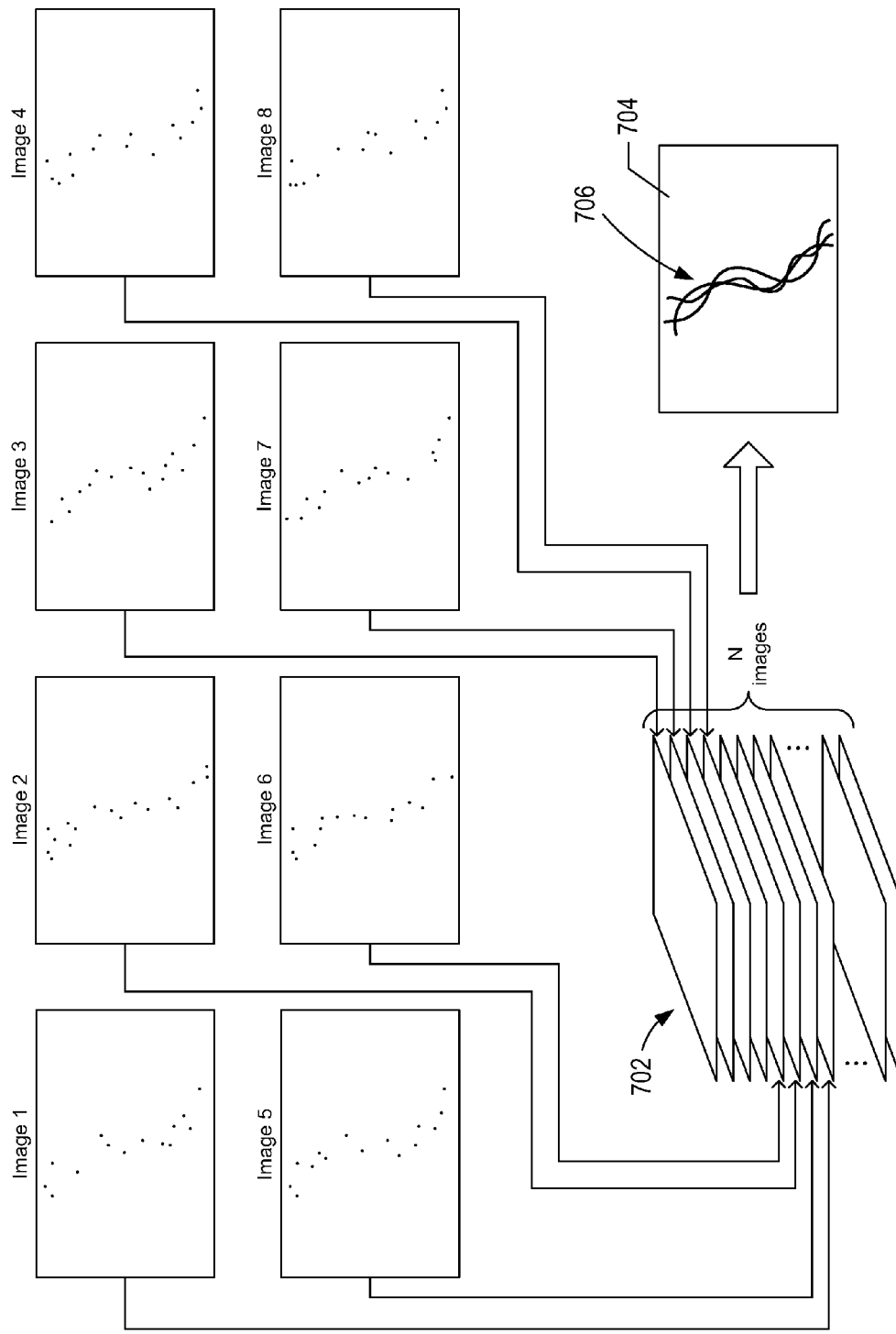
FIG. 7 shows an example of super-resolution fluorescence microscopy to obtain a final super-resolution image.

FIG. 7 shows an example of super-resolution fluorescence microscopy that can be used to obtain a final super-resolution image a specimen. The specimen is labeled with fluorophores of sufficient density to ensure that, when the positions of the fluorophores are accurately determined, those positions will together produce an image of a structure, component, or organelle of interest to the fluorescence microscopist. Then, the specimen is immobilized and a number of intermediate images are generated from the specimen by, for each intermediate image, activating a small subset of the fluorophores and exciting fluorescent emission from the activated fluorophores, as described above with reference to FIG. 6. Only subsets of the fluorophores are activated in order to sufficiently separate fluorophores from one another to satisfy the above-discussed separation constraint. Initially, the fluorophores are in a non-fluorescing, dark state. The specimen is weakly illuminated with a frequency of light that converts a subset of the fluorophores from the dark state to an active state. Activation of a small subset of the fluorophores is stochastic in nature. Activation is carried out with a weak illumination in order to ensure that the average spacing between fluorophores is significantly greater than the diffraction-limited distance (i.e., 200 nm), so that no two activated fluorophores are sufficiently closely spaced that their Airy disk images overlap to the extent that the central peaks cannot be resolved, as discussed above with reference to FIG. 5, and therefore centroids for the fluorophore positions cannot be accurately computed. The specimen is then illuminated with excitation light that causes the activated fluorophores to fluoresce. Following data collection for an intermediate image, the active fluorophores are then illuminated with a bright light of the specific wavelength most effective to bleach the active fluorophores, so that they cannot be again activated and do not fluoresce during data collection for subsequent intermediate images as described above with reference to FIG. 1. As shown in FIG. 7, for example, each of intermediate images 1-8 are produced by collecting data from a different set of sparsely arranged, activated fluorophores. In other words, each of the intermediate images 1-8 is obtained and processed as described above with reference to FIG. 6. The intermediate images are then summed together 702 to produce a final, composite super-resolution image 704 that reveals a fluorophore-labeled structure, organelle, cellular component, or other feature 706 in the specimen.

Figure 8:
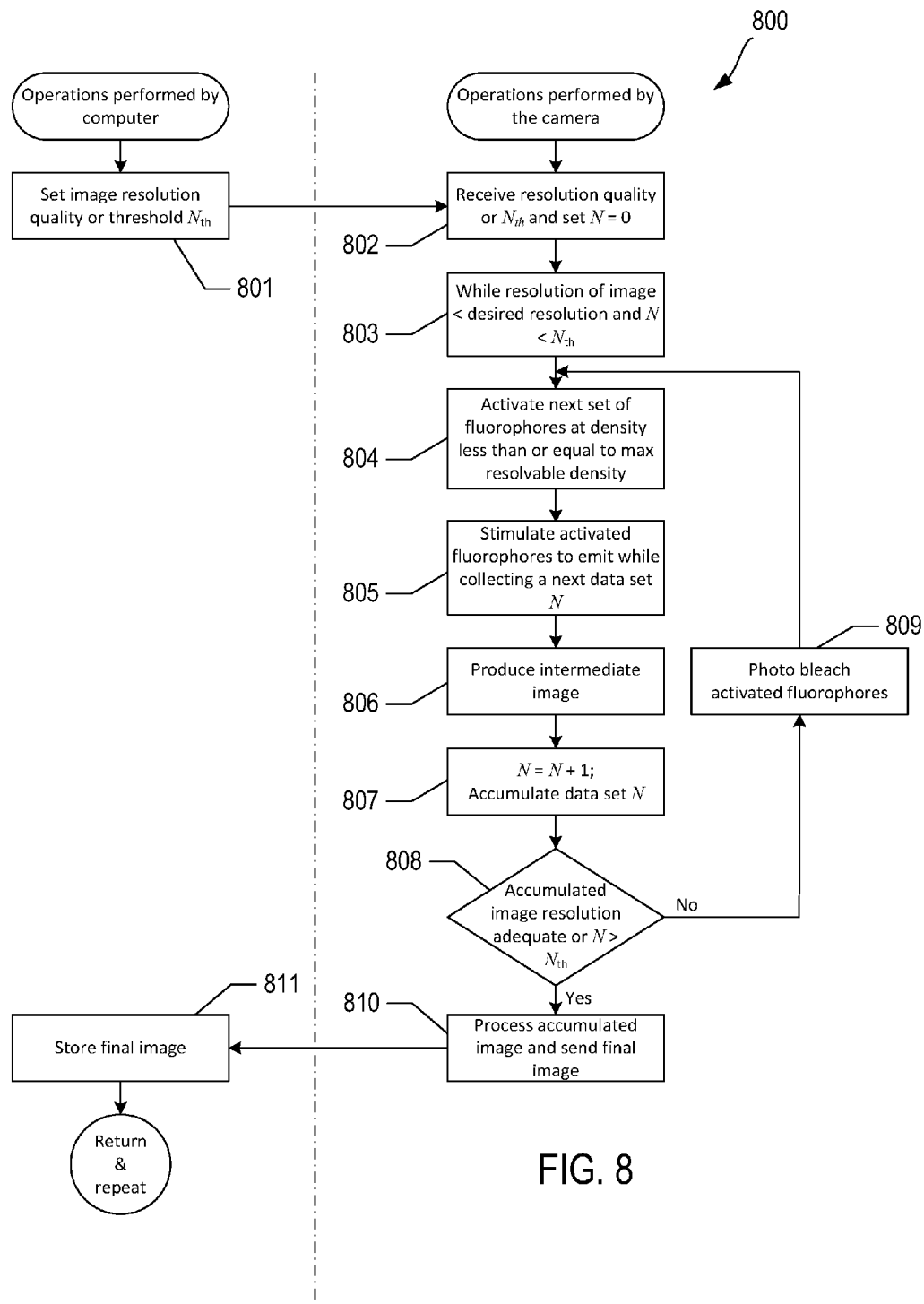
FIG. 8 shows a control-flow diagram of an example super-resolution method to be executed by a camera and a computer of a fluorescence microscope.

FIG. 8 shows a control-flow diagram 800 of an example method of super-resolution microscopy executed by a camera. With this method, intermediate image data acquisition, image processing to produce a final super-resolution image, sending and receiving data from the computer, and operation of the light source is carried out by the camera. In block 801, the method directs the computer to prompt a fluorescent microscope operator to supply a resolution quality for a final super-resolution image or the method directs the computer to prompt the operator for a threshold parameter $N_{th}$, where $N_{th}$ represents the total number of intermediate images to be captured to produce the final super-resolution image. The computer activates the camera and sends the resolution quality or threshold parameter $N_{th}$ to the camera. The camera then executes the operations now described with reference to blocks 802-810. In block 802, an intermediate image index N is initialized to zero. In the while-loop of blocks 803-809, a number of intermediate images, as discussed above with reference to FIGS. 6-7, are produced. In each iteration of the while-loop of steps 804-809, a next set of fluorophores is activated, in block 804, with the density of the activated fluorophores less than or equal to the maximum resolvable density discussed above with reference to FIGS. 6-7. In block 805, fluorescent emission from the activated fluorophores is excited, and a next data set is collected, over time. In block 806, an intermediate image is produced from the collected data by analyzing the data to find the centroids of the point-source images, as discussed above with reference to FIG. 6. In block 807, the intermediate image is summed with previously accumulated or recorded intermediate images to produce a super-resolution image, as described above with reference to FIG. 7, or the image index is incremented. In block 808, when sufficient data has been accumulated to generate a final image of adequate resolution, or the number of intermediate images produced exceeds the threshold $N^{th}$, the method proceeds to block 810, otherwise the method proceeds to block 809 and blocks 804-808 are repeated. In block 809, the activated fluorophores are brightly illuminated by light of an appropriate wavelength to bleach the activated fluorophores, removing that set of fluorophores from subsequent intermediate images. In block 810, a final super-resolution image is produced, as discussed above with reference to FIG. 7, and the super-resolution imaging process terminates by transmitting the final image to the computer. In block 811, the computer stores the final image.

Figure 9:
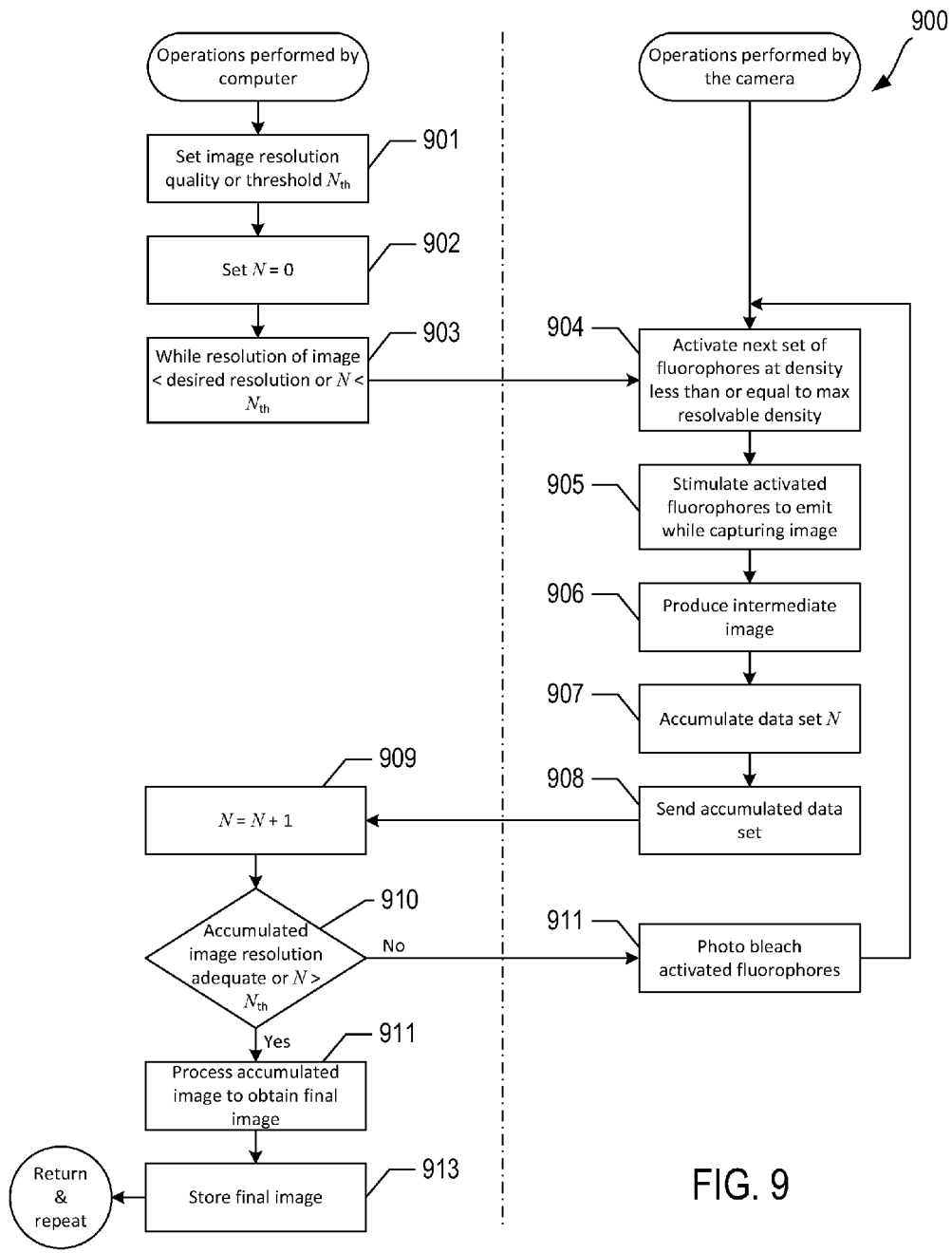
FIG. 9 shows a control-flow diagram of an example super-resolution method to be executed by a camera and a computer of a fluorescence microscope.

FIG. 9 shows a control-flow diagram 900 of an example method of super-resolution microscopy executed by a camera and a computer of a microscopy instrument. With this method, execution of task is divided between the camera and the computer. In particular, intermediate image acquisition and control over operation of the light source is carried out by the camera, while a final super-resolution image is selected by the computer. In block 901, the method directs the computer to prompt a fluorescent microscope operator to supply a resolution quality for a final super-resolution image or the method directs the computer to prompt the operator for a threshold parameter $N_{th}$, where $N_{th}$ represents the total number of intermediate images to be captured to produce the final super-resolution image. In block 902, an intermediate image index N is initialized to zero. In the while-loop of blocks 903-909, execution of the method switches over to the camera with a number of intermediate images is to be produced by the camera, as discussed above with reference to FIGS. 6-7, and the data associated with the images is accumulated or recorded in memory by the camera. In each iteration of the while-loop of steps 904-908, a next set of fluorophores is activated, in block 904, with the density of the activated fluorophores less than or equal to the maximum resolvable density discussed above with reference to FIGS. 6-7. In block 905, fluorescent emission from the activated fluorophores is excited, and a next data set is collected, over time. In block 906, an intermediate image is produced from the collected data by analyzing the data to find the centroids of the point-source images, as discussed above with reference to FIG. 6. In block 907, the intermediate image is summed with previously accumulated intermediate images to produce a super-resolution image, as described above with reference to FIG. 7. In block 908, the super-resolution image is sent from the camera to the computer. In block 909, the computer increments the index N. In block 910, when sufficient data has been accumulated to generate a final image of adequate resolution, or the number of intermediate images produced exceeds the threshold $N^{th}$, the method proceeds to block 911, otherwise the method proceeds to block 912 in which activated fluorophores are brightly illuminated by light of an appropriate wavelength to bleach the activated fluorophores, removing that set of fluorophores from subsequent intermediate and blocks 904-908 are repeated. In block 911, accumulated intermediate image data is further processed to produce a final super-resolution image, as discussed above with reference to FIG. 7. In block 911, the computer stores the final image and the super-resolution imaging process terminates.

Figure 10:
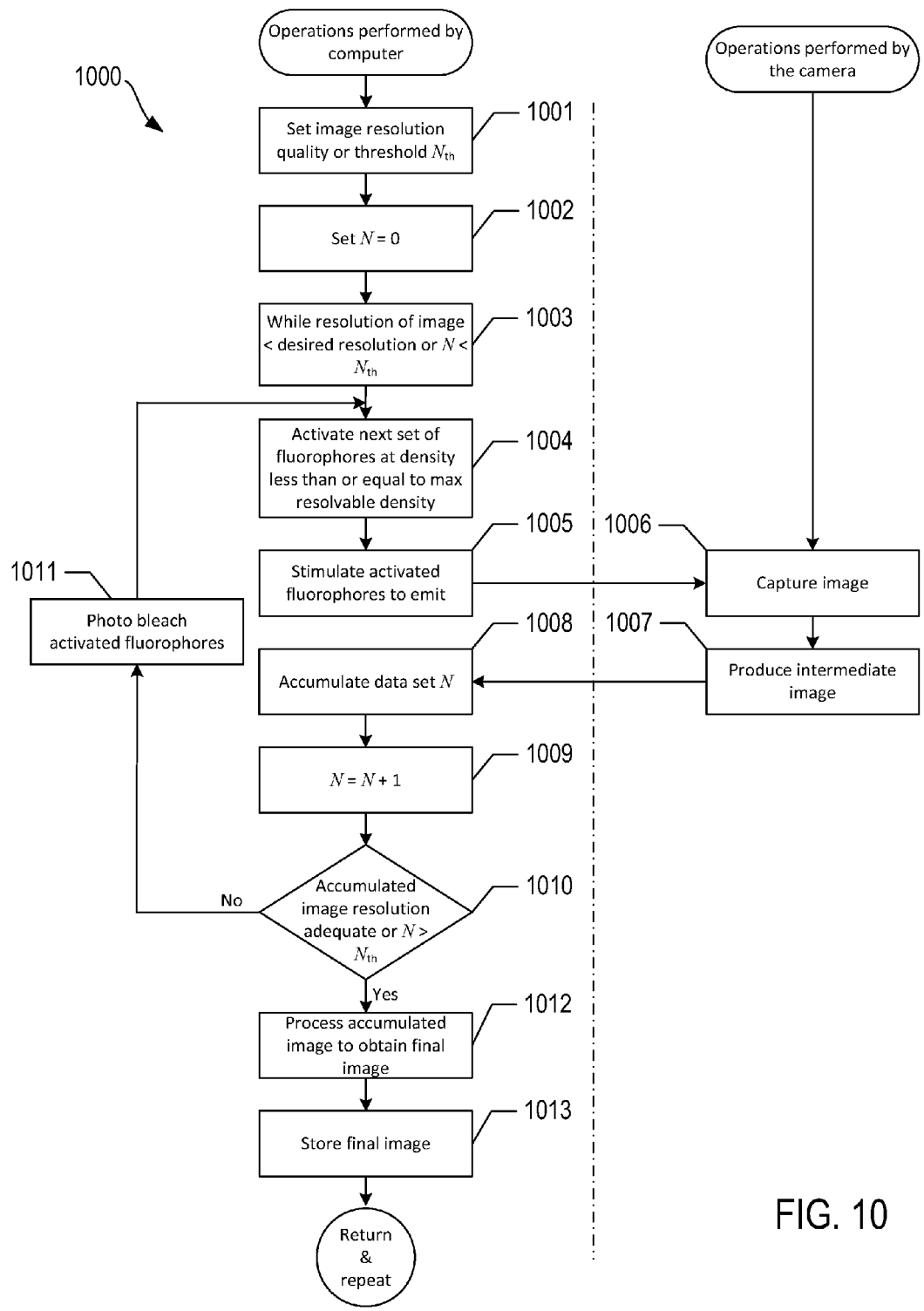
FIG. 10 shows a control-flow diagram of an example super-resolution method to be executed by a camera and a computer of a microscopy instrument.

In alternative embodiments, the image capture and production of intermediate images can be carried out by the camera, while control of the light source, accumulation of the intermediate image data, and processing the accumulated image data to produce a final image are carried out by the computer. FIG. 10 shows a control-flow diagram 1000 of an example method of super-resolution microscopy executed by a camera and a computer of a microscopy instrument. In block 1001, the method directs the computer to prompt a fluorescent microscope operator to supply a resolution quality for a final super-resolution image or the method directs the computer to prompt the operator for the threshold parameter $N_{th}$. In block 1002, an intermediate image index N is initialized to zero. In each iteration of the while-loop of blocks 1003-1010, a next set of fluorophores is activated, in block 1004, with the density of the activated fluorophores less than or equal to the maximum resolvable density discussed above with reference to FIGS. 6-7. In block 1005, fluorescent emission from the activated fluorophores is excited. In blocks 1006 and 1007, execution of the method switches to the camera. In block 1006, an image of the specimen is captured, and in block 1007, the image is processed to produce an intermediate image by analyzing the image data to find the centroids of the point-source images, as discussed above with reference to FIG. 6. In block 1008, the computer stores and sums the intermediate image created by the camera with previously accumulated intermediate images to produce a super-resolution image, as described above with reference to FIG. 7. In block 1009, the image index is incremented. In block 1010, when sufficient data has been accumulated to generate a final image of adequate resolution, or the number of intermediate images produced exceeds the threshold $N^{th}$, the method proceeds to block 1012, otherwise the method proceeds to block 1011 in which activated fluorophores are brightly illuminated by light of an appropriate wavelength to bleach the activated fluorophores, removing that set of fluorophores from subsequent intermediate images and blocks 1004-1010 are repeated. In block 1012, accumulated intermediate image data is further processed to produce a final super-resolution image, as discussed above with reference to FIG. 7. In block 1013, the computer stores the final image and the super-resolution imaging process terminates.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated.

It is intended that the scope of this disclosure be defined by the following claims and their equivalents:

1. A fluorescence microscopy instrumentation system, the system comprising:
   a light source to emit an activation beam of light and an excitation beam of light;
   an objective lens to receive and direct the activation and excitation beams into a specimen labeled with light emitters comprising a number of subsets of light emitters; and
   a camera to capture light emitted from each subset of the light emitters to record an unprocessed intermediate image for said each subset of the light emitters,
   the camera to further process the recorded intermediate images and provide processed images to be summed to produce a final super-resolution image of the specimen, and
   wherein the activation beam of light converts said each subset of the light emitters into an active state and the excitation beam of light converts said each subset of light emitters from the active state into a fluorescent state to emit light.

2. The system of claim 1, wherein the camera is in communication with the light source to repeatedly direct the light source to illuminate the specimen with the activation beam and the excitation beam, and wherein the camera is to record, over time, the unprocessed intermediate image for each subset of the light emitters.

3. The system of claim 1, wherein the camera is to direct the light source to photo bleach said each subset of light emitters after capture of each unprocessed intermediate image.

4. The system of claim 1, wherein the activation beam is a low intensity beam to stochastically convert said each subset of light emitters into the active state.

5. The system of claim 1, wherein the light emitters are fluorophores that are activated when illuminated by the activation beam and are excited to emit fluorescent light when illuminated by the excitation beam.

6. The system of claim 1, wherein the activation beam of light is of a first frequency and the excitation beam of light is of a second frequency that is different from the first frequency.

7. The system of claim 1, wherein the camera comprises a digital signal processor to process the recorded intermediate images.

8. The system of claim 1, wherein the camera comprises a graphics processing unit to process the recorded intermediate images.

9. The system of claim 1, wherein the camera comprises one or more processors to process the recorded intermediate images.

10. The system of claim 1, wherein the camera comprises an application-specific integrated circuit to process the recorded intermediate images.

11. The system of claim 1, further comprising a computer, wherein the computer is in communication with the light source to repeatedly direct the source to illuminate the specimen with the activation beam and the excitation beam.

12. The system of claim 11, whereby processing of the recorded intermediate images uses the camera in combination with the computer.

13. The system of claim 11, wherein the computer is to direct the light source to photo bleach said each subset of light emitters after capture of each unprocessed intermediate image.

14. A method for producing a final super-resolution image of a specimen, the method comprising:
    illuminating at least a portion of the specimen to convert a subset of light emitters within the specimen into an active state;
    exciting the subset of light emitters in the active state into a fluorescent state to emit light;
    capturing light emitted from the subset of light emitters to record an unprocessed intermediate image of the subset of light emitters using a camera;
    photobleaching the subset of light emitters;
    repeating illuminating, exciting, capturing, and photobleaching steps for a different subset of light emitters; and
    using the camera to process the recorded intermediate images and provide processed images for producing the final super-resolution image.

15. The method of claim 14, wherein illuminating the at least a portion of the specimen to convert light emitters into the active state further comprises the camera directing a light source to emit an activation beam into the specimen.

16. The method of claim 14, wherein illuminating the at least a portion of the specimen to convert light emitters into the active state further comprises illuminating the specimen with a low intensity beam to stochastically convert the subset of light emitters into the active state.

17. The method of claim 14, wherein exciting the light emitters in the active state into the fluorescent state further comprises the camera directing a light source to emit an excitation beam into the specimen, wherein the excitation beam converts the light emitters in the active state into the fluorescent state to emit light.

18. The method of claim 14, wherein photobleaching the subset of light emitters further comprises the camera directing a light source to illuminate the specimen with light of an appropriate wavelength to photobleach the subset of light emitters in the active state to remove the subset of light emitters in the active state from subsequent intermediate images.

19. The method of claim 14, wherein using the camera to process the recorded intermediate images for producing the final super-resolution image comprises the camera summing the processed images to produce the final super-resolution image.

20. The method of claim 14, wherein illuminating at least a portion of the specimen to convert the subset of light emitters within the specimen into the active state further comprises illuminating the specimen with light of a first frequency, and exciting the light emitters in the active state into the fluorescent state further comprises illuminating the specimen with light of a second frequency.

21. The method of claim 14, wherein illuminating the at least a portion of the specimen to convert the subset of light emitters into the active state further comprises a computer directing a light source to emit an activation beam into the specimen.

22. The method of claim 14, wherein exciting the light emitters in the active state into the fluorescent state further comprises a computer directing a light source to emit an excitation beam into the specimen, wherein the excitation beam converts the light emitters in the active state into the fluorescent state to emit light.

23. The method of claim 14, wherein photobleaching the subset of light emitters further comprises a computer directing a light source to illuminate the specimen with light of an appropriate wavelength to photobleach the light emitters in the active state to remove the subset of light emitters in the active state from subsequent intermediate images.

24. The method of claim 14, wherein processing the recorded intermediate images for producing the final super-resolution image comprises using a computer to sum the processed images to produce the final super-resolution image.

25. A camera comprising:
    one or more processors; and
    a computer-readable medium having machine-readable instructions recorded thereon,
    wherein the one or more processors is configured to execute the machine-readable instructions for:
        directing a light source to illuminate at least a portion of a specimen to convert a subset of light emitters within the specimen into an active state;
        directing the light source to excite the subset of light emitters in the active state into a fluorescent state to emit light;
        capturing light emitted from the subset of light emitters to record an unprocessed intermediate image of the subset of light emitters in the camera;
        directing the light source to illuminate the specimen to photobleach the subset of light emitters;
        repeating illuminating, exciting, capturing and photobleaching to record a number of subsequent unprocessed intermediate images in the camera, each subsequent intermediate image corresponding to a different subset of light emitters; and
        using the camera to process the recorded intermediate images and provide processed images for producing a final super-resolution image of the specimen.

26. The camera of claim 25, wherein the one or more processors comprises a digital signal processor to process the recorded intermediate images.

27. The camera of claim 25, wherein the one or more processors comprises a graphics processing unit to process the recorded intermediate images.

28. The camera of claim 25, wherein the one or more processors comprises an application-specific integrated circuit to process the recorded intermediate images.

29. The camera of claim 25, wherein the processed images are to be summed to produce the final super-resolution image of the specimen.

* * * * *